United States Patent
Okuda et al.

Patent Number: 6,120,474
Date of Patent: Sep. 19, 2000

[54] BLOOD COMPONENT-RECOVERING APPARATUS AND A METHOD FOR RECOVERING BLOOD COMPONENTS USING THE SAME

[75] Inventors: Morihiro Okuda; Nobuo Takagi; Daisuke Fukuta, all of Osaka, Japan

[73] Assignee: Nissho Corporation, Osaka, Japan

[21] Appl. No.: 09/210,571

[22] Filed: Dec. 14, 1998

[30] Foreign Application Priority Data

Dec. 15, 1997 [JP] Japan .................................... 9-344585
Dec. 26, 1997 [JP] Japan .................................... 9-358766

[51] Int. Cl.⁷ .................................................. A61M 37/00
[52] U.S. Cl. ...................... 604/4.01; 604/6.02; 604/6.03; 210/446
[58] Field of Search ............................ 604/4.01, 5, 6.02, 604/7, 6.03; 210/446, 645, 654, 655, 805, 806

[56] References Cited

U.S. PATENT DOCUMENTS 3,747,769  7/1973  Brumfield ................................ 210/350
4,416,777  11/1983 Kuroda et al. .......................... 210/446

FOREIGN PATENT DOCUMENTS 0 806 475 A2  11/1997  European Pat. Off. .

OTHER PUBLICATIONS

Patent Abstract of Japan; vol. 003, No. 142, JP 54–122714 A; Publ. date Sep. 22, 1979.

*Primary Examiner*—John B. Yasko
*Attorney, Agent, or Firm*—Kubovcik & Kubovcik

[57] ABSTRACT

The present invention provides a blood component-recovering apparatus and a method for high-yield recovery of leukocytes captured in a filter of the blood component-recovering apparatus. The blood component-recovering apparatus includes a housing accommodating (a) a filtration portion charged with (b) a filter which is capable of passing erythrocytes but capturing leukocytes and (c) a pressing member for pressing the filter, the housing being provided in the sidewall thereof with (d) a blood flow inlet and (e) a blood flow outlet communicating with the filtration portion. The housing of the blood component-recovering apparatus is further provided in the upper wall thereof with (f) a means capable of transferring, or moving, the pressing member vertically. The pressing member of the blood component-recovering apparatus is transferred downward while a blood containing blood components is passed through the filtration portion. The pressing member is then transferred upward to increase the volume of the filtration portion, and a washing solution is then passed through the filter to recover leukocytes.

20 Claims, 4 Drawing Sheets

BLOOD COMPONENT-RECOVERING APPARATUS AND A METHOD FOR RECOVERING BLOOD COMPONENTS USING THE SAME

FIELD OF THE INVENTION

The present invention relates to an apparatus for recovering blood components such as leukocytes from blood containing the blood components and in particular to an apparatus for recovering hematopoietic stem cell- and/or hematopoietic precursor cell-derived leukocytes from umbilical cord blood, bone marrow blood, peripheral blood etc., and a method of recovering blood components using the same.

BACKGROUND OF THE INVENTION

Blood preparations from which leukocytes have been removed have been utilized in blood transfusion in order to prevent non-hemolytic fever reactions such as fever, chill, itching etc. These reactions occur as side effects of blood transfusion, especially, in treatment of patients who frequently undergo blood transfusion, which result from allogeneic immunoreaction by leukocytes. Such blood preparations from which leukocytes have been removed have been produced by a centrifugation method utilizing the difference in specific gravity among blood components, or a recovery method of using a leukocyte-removing filter and the like. Among these, the method of using a leukocyte-removing filter has been used widely because blood preparations from which leukocytes are removed to a high degree can be obtained in a simple operation. Leukocytes adsorbed onto the filter were discarded along with the filter.

Meanwhile, bone marrow transplant therapy and peripheral blood stem cell transplant therapy have been applied to a hematopoietic malady occurring when chemotherapy was conducted for leukemia, cancer etc., wherein hematopoietic stem cells and hematopoietic precursor cells contained in bone marrow blood and peripheral blood have been transplanted in patients in order to overcome the hematopoietic obstacles. Further, it was found in recent years that hematopoietic stem cells and/or hematopoietic precursor cells are also contained in umbilical cord blood, and therapy by transplanting umbilical cord blood stem cells is also expected to be a promising method.

For preparing hematopoietic stem cells and hematopoietic precursor cells from a blood containing these blood components, cryopreserved blood cells are thawed to be transplanted into patients with hematopoietic obstacles (WO 96/17514). If cryopreserved blood is contaminated with erythrocytes, after the blood is thawed the erythrocytes are lyzed to cause side effects. Therefore, the erythrocytes should previously be removed from blood before freezing.

In addition, removal of platelets from blood has not been a problem so far, but in removing cells as a cause of complications in homotransplantation and removing cancer cells in autotransplantation in recent years, platelets cause aggregation and adhesion of these cells to reduce separation efficiency, so removal of platelets from blood is also desirable.

Heretofore, there is known a method of obtaining leukocytes from whole blood in which a leukocyte separation filter consisting of a fibrous material is contacted with a plasma, and a blood cell-floating fluid is passed therethrough to be separated into erythrocytes and other blood components, and the leukocytes captured in the leukocyte separation filter are recovered (Japanese Patent Publication No. 54131/1983). Further, Japanese Laid-Open Patent Publication No. 104,643/1996 discloses a method of recovering hematopoietic stem cell- and hematopoietic precursor cell-derived, erythrocyte- and platelet-free leukocytes from a blood, i.e., bone marrow blood or peripheral blood. The method comprises passing a cell population containing erythrocytes, hematopoietic stem cells and hematopoietic precursor cells through a filter which is capable of passing erythrocytes but capable of capturing leukocytes, causing a fluid flow in the opposite direction to the passing fluid, and recovering the captured leukocytes. In addition, Japanese Laid-Open Patent PublicationNo. 121,849/1987 discloses a method of obtaining hematopoietic stem cells, which comprises passing a cell population containing erythrocytes, hematopoietic stem cells, monocytes and granulocytes through a first capturing means which is capable of passing erythrocytes but capturing leukocytes, recovering the captured leukocytes in a recovery solution, passing the recovered leukocytes through a second capturing means which is capable of capturing monocytes and granulocytes but passing hematopoietic stem cells, and obtaining hematopoietic stem cells from said capturing means.

In these methods of recovering leukocytes captured in the filter described in said references, however, the method of passing a recovering solution in the same direction as that of the first passing solution requires raising the liquid pressure of the recovering solution in order to wash out leukocytes captured in the fibers, thus making it difficult to recover leukocytes in high yield. The method of recovering leukocytes captured by causing a fluid flow in the opposite direction to the first passing fluid permits spaces between the fibers to be disordered thus achieving a higher yield of leukocytes than the method of passing a fluid flow in the same direction as the first passing fluid, but nevertheless the captured leukocytes cannot sufficiently be recovered.

An object of the present invention is to provide an apparatus for high-yield recovery of leukocytes captured in a filter and a method for recovering leukocytes using the same.

SUMMARY OF THE INVENTION

That is, the present invention relates to a blood component-recovering apparatus comprising a housing accommodating (a) a filtration portion charged with (b) a filter which is capable of passing erythrocytes but capturing leukocytes and (c) a pressing member for pressing said filter, the housing being provided in the sidewall thereof with (d) a blood flow inlet and (e) a blood flow outlet communicating with said filtration portion. The housing of said blood component-recovering apparatus is further provided in the upper wall thereof with (f) a means capable of transferring, or moving, the pressing member vertically. The pressing member of said blood component-recovering apparatus is transferred to a downward position and a blood containing desired blood components is passed through the filtration portion. The pressing member is then transferred upward to increase the volume of said filtration portion, and a washing solution is then passed to recover leukocytes.

One embodiment of this invention is a blood component-recovering apparatus comprising a housing accommodating (a) a filtration portion charged with (b) a filter which is capable of passing erythrocytes but capturing leukocytes and (c) a pressing member for pressing said filter, the housing being provided in the [sidewalk] sidewall thereof with (d) a blood flow inlet and (e) a blood flow outlet communicating with said filtration portion, and further being provided in the upper wall thereof with (f) a means capable of transferring the pressing member vertically, wherein (c) said pressing member is in a downward position while a blood containing blood components is passed through the filtration portion, and is then transferred upward to increase the volume of said filtration portion.

Another embodiment of this invention is a blood component-recovering apparatus comprising a housing accommodating (a) a filtration portion charged with (b) a filter which is capable of passing erythrocytes but capturing leukocytes and (c) a pressing member for pressing said filter, the housing being provided in the sidewall thereof with (d) a blood flow inlet and (e) a blood flow outlet communicating with said filtration portion, and further being provided in the upper wall thereof with (f) a means capable of transferring the pressing member vertically, wherein (c) said pressing member is transferred to a downward position and a blood containing blood components is passed through the filtration portion. The pressing member is then transferred upward to increase the volume of said filtration portion, and wherein (f) said means capable of transferring the pressing member vertically comprises (g) a bolt portion consisting of (h) a rod-shaped member having (i) a male screw formed on the sidewall thereof extending in a longitudinal direction above the pressing member, and (j) a hole through which the rod-shaped member can be transferred vertically being formed in the bottom of (k) a concave portion on the upper wall of the housing, and (l) a nut portion having (m) a female screw formed on the inner wall of a cylinder, said nut portion having an outer diameter permitting the cylinder to be inserted into said concave portion and capable of being screw-engaged with the male screw in said bolt portion.

Another embodiment of this invention is a blood component-recovering apparatus comprising a housing accommodating (a) a filtration portion charged with (b) a filter which is capable of passing erythrocytes but capturing leukocytes and (c) a pressing member for pressing said filter, the housing being provided in the sidewall thereof with (d) a blood flow inlet and (e) a blood flow outlet communicating with said filtration portion, and being further provided in the upper wall thereof with (f) a means capable of transferring the pressing member vertically, wherein (c) said pressing member is transferred downward while a blood containing desired blood components is passed through the filtration portion, then transferred upward to increase the volume of said filtration portion, and wherein (f) said means capable of transferring the pressing member vertically consists of (n) a rod-shaped member extending in a longitudinal direction above the pressing member, having (o) a lock portion at the bottom and having (p) a male screw formed on the sidewall thereof, (q) a chamber being provided on the pressing member, having (r) a first hole through which said rod-shaped member penetrates and accommodating said lock portion, and (s) a female screw being formed on the inner wall of (t) a second hole provided on the upper wall of housing and capable of being screw-engaged with the male screw of said rod-shaped member. The pressing member of this invention may have the shape of a disk provided in a side edge thereof with (u) an O-ring capable of sliding liquidtightly along the inner wall of the housing.

Another embodiment of this invention is a blood component-recovering apparatus having a housing comprising (v) an upper lid portion and (w) a lower lid portion, wherein (v) the upper lid portion accommodates (x) a spring body for pressing (a) a filtration portion charged with (b) a filter which is capable of passing erythrocytes but capturing leukocytes and (c) a pressing member is connected to the end of said spring body and is capable of being transferred to the inside of (w) a lower lid portion, and (w) said lower lid portion accommodates (c) said filtration portion, is provided with (d) a blood inlet and (e) a blood outlet and is screw-engaged or fitted to the upper lid portion.

Another embodiment of this invention is a blood component-recovering apparatus having a housing comprising (v) an upper lid portion and (w) a lower lid portion, wherein (v) an upper lid portion accommodates (x) a spring body for pressing (a) a filtration portion charged with (b) a filter which is capable of passing erythrocytes but capturing leukocytes, and (w) the lower lid portion accommodates (a) said filtration portion and (c) a pressing member placed on (a) the filtration portion, and is provided with (d) a blood inlet and (e) a blood outlet and is screw-engaged or fitted to the upper lid portion.

The outer wall of the lower lid portion is provided with protruding portion, and the sidewall of the upper lid portion is provided with a hole portion consisting of a lengthwise long hole extending in a longitudinal direction and at least one crosswise long hole communicating with said lengthwise long hole, wherein the protruding portion slides along the lengthwise long hole and is locked with the crosswise long hole.

Further, the present invention is a method of recovering blood components, which comprises passing a blood containing blood components through a filtration portion charged with a filter which is capable of passing erythrocytes but capturing leukocytes, further enlarging or increasing the inner volume of said filtration portion, and passing a washing solution to recover leukocytes.

DETAILED DESCRIPTION OF THE INVENTION

Figure 1:
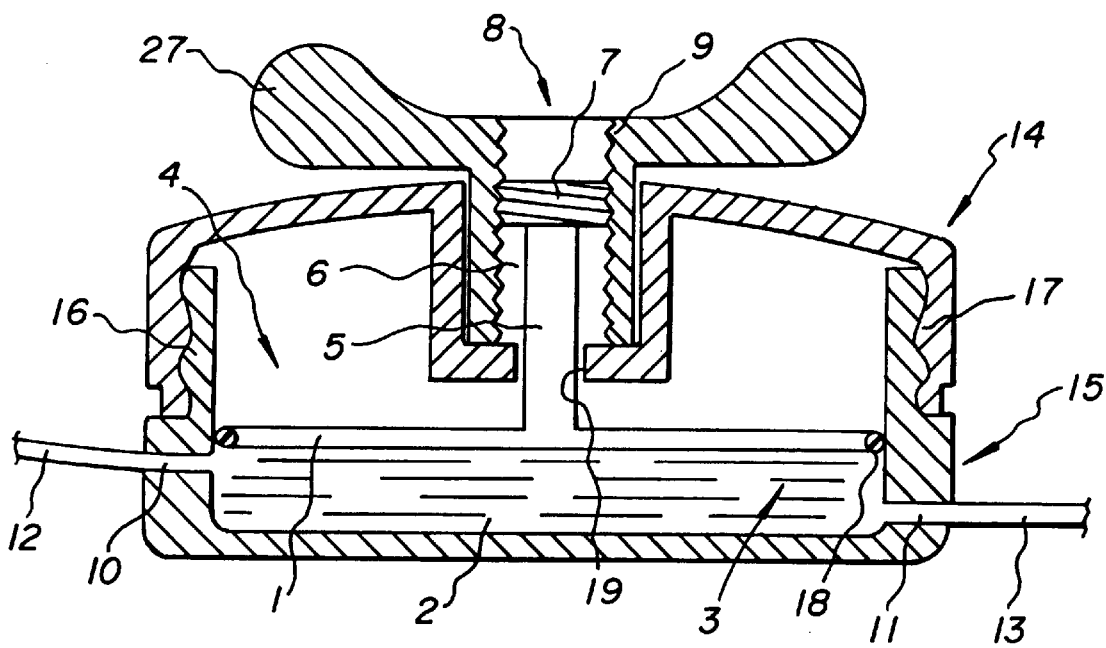
FIG. 1 is a schematic view showing one example of the blood component-recovering apparatus of the present invention.

The filter capable of passing erythrocytes but capturing leukocytes in the present invention is a fibrous or porous aggregate, for instance, synthetic fibers such as polyester, polyamide, polyacrylonitrile fiber etc., regenerated fibers such as cellulose, cellulose acetate fiber etc., inorganic fibers such as glass fiber etc., natural fibers such as cotton fiber etc., porous materials such as a foamed molded article, sintered material, etc., spherical materials such as hydroxyapatite beads, etc. If erythrocytes as well as platelets are intended to be passed through the filter, the surface of the aggregate constituting said filter is coated with a polymer of a non-ionic hydrophilic group-containing compound such as hydroxyethyl methacrylate and a basic nitrogenous functional group-containing compound such as diethylaminoethyl methacrylate, as described in Japanese Patent Publication No. 51060/1994. Otherwise, fibers constituting the filter are obtained from a polymer copolymerized or graft-copolymerized with a hydroxyl group-containing compound or a methacrylate group-containing compound and other polymerizable compounds, as described in Japanese Laid-Open Patent Publication No. 249063/1989.

If the filter is composed of a fiber aggregate, the fiber diameter is 25 μm or less, preferably 10 μm or less, and more preferably 0.5 to 3 μm. If the fiber diameter exceeds 25 μm, the yield of leukocytes captured in the filter tends to decrease. The bulk density of the fiber aggregate ranges from 0.05 to 0.50 g/cm³, preferably 0.08 to 0.30 g/cm³, and more preferably 0.10 to 0.20 g/cm³. If the bulk density is less than 0.05 g/cm³, the yield of leukocytes captured in the filter tends to decrease, while if the bulk density exceeds 0.50 g/cm³, the flow rate of blood passing through the filter tends to decrease. The bulk density of the filter means the bulk density before enlarging the volume of the filtration portion.

If the filter is composed of a multi-layer fiber aggregate, at least one layer has a fiber diameter of 25 μm or less and a bulk density of 0.05 to 0.50 g/cm³. The multi-layer structure is composed of 2 to 6 layers, where a layer adjacent to the blood flow inlet having a large fiber diameter and a high bulk density and a layer adjacent to the blood flow outlet having a small fiber diameter and a low bulk density are preferably arranged so that leukocytes can be captured in the order of a decreasing diameter through the layers. If the filter is a multi-layer fiber aggregate consisting of a fiber aggregate with a fiber diameter of 10 μm and a bulk density of 0.23 g/cm³ as a first layer, a fiber aggregate with a fiber diameter of 3.5 μm and a bulk density of 0.11 g/cm³ as a second layer and a fiber aggregate with a fiber diameter of 1.5 μm and a bulk density of 0.12 g/cm³ as a third layer, then blood components with large diameters will be captured by the first layer, monocytes and granulocytes by the second layer and lymphocytes by the third layer. If the filter material consists of a porous material, its pore diameter ranges preferably from 1 to 500 μm.

The blood which can be treated according to the present invention includes human blood, animal blood, bone marrow blood, peripheral blood, umbilical cord blood, etc. and the blood components include monocytes, granulocytes, lymphocytes, leukocytes derived from hematopoietic stem cells or hematopoietic precursor cells, erythrocytes, platelets, etc.

The washing solution is preferably physiological saline, Hank's solution (HBSS), a buffer solution such as Dulbecco phosphate buffer (D-PBS) etc., which may optionally contain proteins such as human serum albumin or an anticoagulation agent.

The present invention provides a blood component-recovering apparatus in which a blood containing these blood components is passed through a filtration portion charged with a filter which is capable of passing erythrocytes but capturing leukocytes, then the inner volume of said filtration portion is increased, and the washing solution is then passed to recover leukocytes. The filter may be charged directly in the filtration portion in the rigid housing, or may be charged in a bag consisting of a flexible resin and having a blood flow inlet tube and a blood flow outlet tube, wherein said bag is accommodated in the filtration portion in the rigid housing. The bag consisting of a flexible resin is charged with the filter in a compressed condition, and the inner volume of the filtration portion is increased by moving the pressing member upward to increase the inner volume of the bag.

The housing may be made of a material including a synthetic resin such as polycarbonate, polystyrene, polyolefin, hard polyvinyl chloride, etc. and metals such as stainless steel, aluminum, etc. The bag is formed by welding two sheets of a flexible resin along the edge thereof, and the end of the edge is provided with rigid ports, that is, a blood flow inlet and a blood flow outlet. The flexible resin constituting the bag includes polyester, polyolefin, polyurethane, ethylene-vinyl acetate copolymers, and soft polyvinyl chloride.

In the present invention, after blood is passed through the inside of the filter, the inner volume of the filtration portion in the housing is increased thus further increasing the inner volume of the filter in the housing, and then the washing solution is passed therethrough to recover leukocytes captured in the filter. The inner volume of the filtration portion after expansion is at least 1.10-fold, preferably 1.20- to 1.80-fold, and more preferably 1.30- to 1.60-fold relative to the inner volume of the filtration portion before the blood is passed through the filter. If the magnification of expansion of the filtration portion is less than 1.10-fold, there is the possibility that leukocytes captured in the filter cannot sufficiently be recovered, while if the magnification is too high, the housing tends to become large.

The blood component-recovering apparatus of the present invention is described with reference to the blood component-recovering apparatus shown in FIG. 1.

FIG. 1 is a schematic view of the blood component-recovering apparatus where an upper lid portion (14) and a lower lid portion (15) are completely screw-engaged to form housing (4), and filter (2) is pressed just before blood is passed. The lower lid portion (15) is provided with a filtration portion (3) accommodating a filter (2), and its sidewall is provided with blood flow inlet (10) and blood flow outlet (11), and the pressing member (1) is placed on the upper part of the filter (2). The pressing member (1) comprises a rod-shaped member (5) extending upward in a longitudinal direction, and the top of the rod-shaped member (5) has a head (7) with a larger diameter than the rod-shaped member (5), and a male screw is formed on the sidewall of the head (7). The upper lid portion (14) is provided with a concave portion (6) on the upper wall of the housing (4), and the bottom of the upper lid portion (14) is provided with a hole (19) through which the rod-shaped member (5) can move vertically.

In this blood component-recovering apparatus, a nut portion (8) is used to transfer the pressing member (1) vertically. The nut portion (8) comprises a cylinder having an outer diameter permitting it to be inserted into the concave portion (6) and has a grasping portion (27) provided with a female screw (9) capable of screw-engagement with the male screw on the head (7) in the inner wall of the cylinder. The pressing member (1) is disk-shaped and provided therearound with an O-ring (18) sliding liquid-tightly along the inner wall of the lower lid portion (15). A female screw (17) is formed on the inner wall of the opening of the upper lid portion (14), and a male screw (16) is formed on the outer wall of the opening of the lower lid portion, and the female screw (17) and the male screw (16) are screw-engaged to form the housing (4). In FIG. 1, the housing (4) is formed by screw-engagement, but may also be formed by adhesion after fitting. Further, in FIG. 1, the rod-shaped member (5) is provided at the top thereof with the head (7) and the male screw is formed on the sidewall of the head (7), but the male screw may be formed on the sidewall of the rod-shaped member (5). In FIG. 1, the nut portion (8) may be provided with a lock so that screw-engagement between the female screw (9) in the nut portion and the male screw in the head (7) in the rod-shaped member (5) is not loosened after fixing.

For recovering leukocytes from a blood by use of the blood component-recovering apparatus in FIG. 1, the nut portion (8) is inserted into the concave portion (6), and the female screw (9) on the nut portion (8) is screw-engaged with the male screw on the head (7) of the bar-shaped member (5), and the nut portion (8) is then rotated to transfer the bar-shaped member (5) downward so that the pressing member (1) presses the filter (2). After the filtration portion (3) reaches a predetermined volume, blood is passed from the blood flow inlet tube (12) through the blood flow inlet (10) to the filter (2) where leukocytes are captured. Thereafter, the nut portion (8) is rotated in the opposite direction to transfer the rod-shaped member (5) upward thereby enlarging the volume of the filtration portion (3), and a washing solution is then passed through the filter (2) so that along with the washing solution, leukocytes captured in the filter (2) flow through the blood flow outlet (11), and are recovered from the blood flow outlet tube (13).

Figure 2:
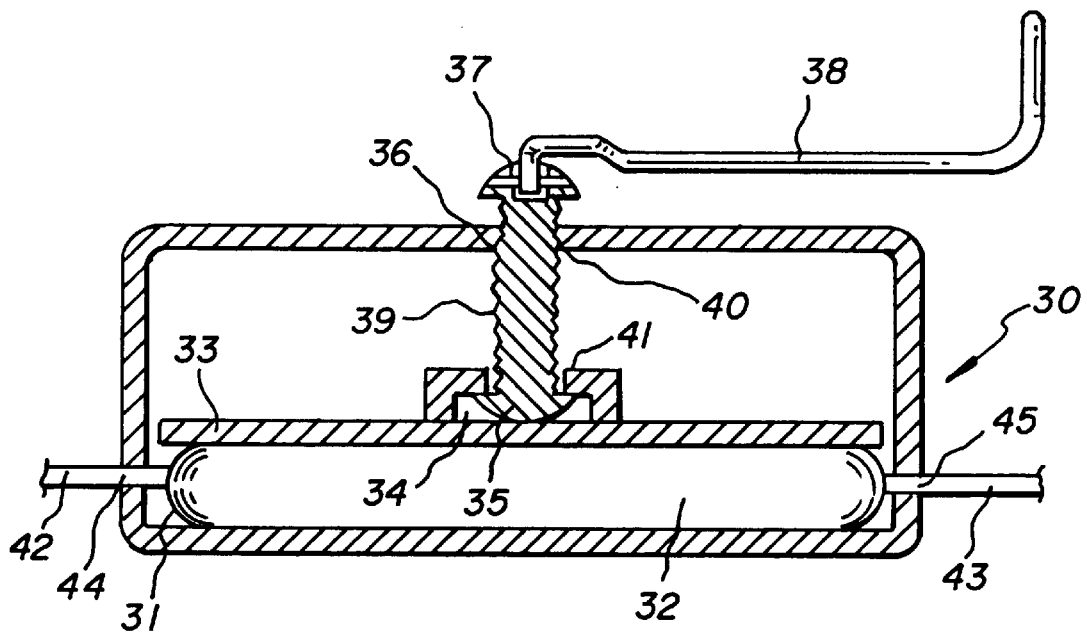
FIG. 2 is a schematic view of another embodiment of the blood component-recovering apparatus of the present invention.

FIG. 2 is a schematic view showing another embodiment of the blood component-recovering apparatus of the present invention, where filter (32) is pressed just before blood is passed. The filter (32) is accommodated in bag (31) made of a flexible resin, and a blood flow inlet tube (42) is connected via bag (31) to a blood flow outlet tube (43). The blood flow inlet tube (42) and blood flow outlet tube (43) are connected to the outside via a blood flow inlet (44) and a blood flow outlet (45) respectively formed on the sidewall of a housing (30). A pressing member (33) is placed on the upper part of the filter (32). The upper part of the pressing member (33) is provided with a chamber (34) having a first hole (41) for accommodating a lock portion (35) and permitting a rod-shaped member (36) to penetrate therethrough. The lock portion (35) is formed at the bottom of the bar-shaped member (36) and possesses a larger diameter than that of the rod-shaped member (36) and can be freely rotated in the chamber (34). The rod-shaped member (36) is provided therearound with a male screw (39) which is screw-engaged with the female screw in a second hole (40) formed on the upper wall of the housing (30) thereby transferring the bar-shaped member (36) vertically. The upper end of the rod-shaped member (36) is provided with a head (37) having a larger diameter than that of the rod-shaped member (36) and connected to a grasping portion (38) for rotating the rod-shaped member (36). In FIG. 2, the periphery of the pressing member (33), unlike the pressing member (1) in FIG. 1 does not necessarily require an O-ring (18) because the filter (32) is accommodated in the bag (31).

To recover leukocytes from blood by use of the blood component-recovering apparatus shown in FIG. 2, the grasping portion (38) is rotated to transfer the rod-shaped member (36) downward to permit the pressing member (33) to press the filter (32). After bag (31) reaches a predetermined volume, blood is passed from the blood flow inlet tube (42) to the bag (31) whereby leukocytes are captured in the filter (32). Thereafter, the grasping portion (38) is rotated in the opposite direction to transfer the rod shaped member (36) upward thereby enlarging the volume of the bag (31), and a washing solution is then passed through the bag (31) whereby leukocytes captured in the filter (32) flow with the washing solution, and are discharged through the blood flow outlet (45) and recovered outside from the blood flow outlet tube (43).

Figure 3:
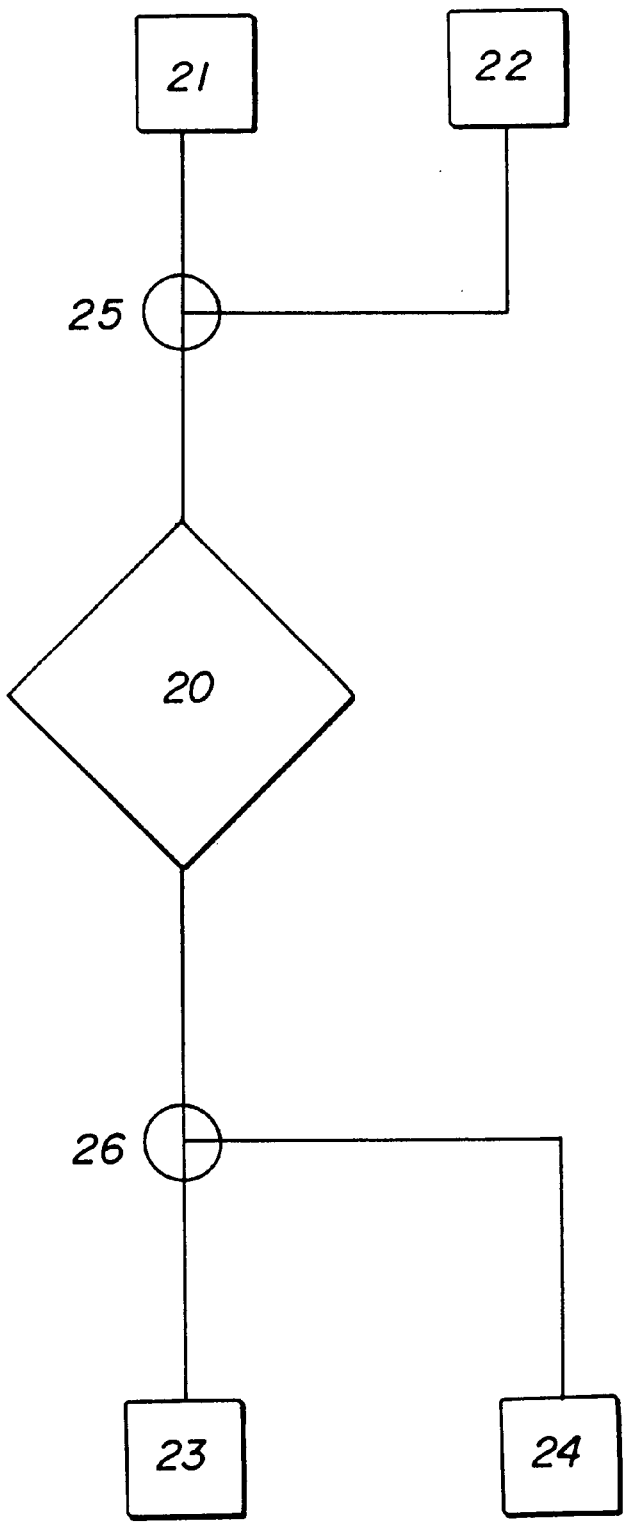
FIG. 3 is a drawing showing the method of the present invention.

FIG. 3 is a drawing showing a method of collecting blood components by use of the blood component-recovering apparatus in FIG. 1.

From a blood bag (21) in which whole blood is accommodated, the whole blood is passed through a 3-directional stopcock (25) to blood component-recovering apparatus (20) in FIG. 3, that is, the whole blood is passed through blood flow inlet tube (12), and introduced to the inside of the filter (2) from the blood flow inlet (10) in the blood component-recovering apparatus in FIG. 1, wherein the filtration portion (3) accommodating the filter (2) has been compressed to a predetermined volume. Leukocytes are captured in the filter (2), e.g., spaces between the fibers therein, while erythrocytes are passed through the fiber aggregate, the blood flow outlet (11), and the blood flow outlet tube (13) of the blood component-recovering apparatus in FIG. 1 and through a 3-directional stopcock (26), and are accommodated in the small blood bag (23) in FIG. 3. The small blood bag (23) can also accommodate platelets in addition to erythrocytes, depending on the type of the filter material.

Then, the grasping portion (27) in FIG. 1 is rotated in the opposite direction to transfer the rod-shaped member (5) upward whereby the volume of the filtration portion (3) is increased. Thereafter, a washing solution in a washing bag (22) is passed through the 3-directional stopcock (25) into the blood component-recovering apparatus (20) in FIG. 3. In this step, it is preferable that introduction of the washing solution into the leukocyte-accommodating bag (24) is temporarily stopped by the 3-directional stopcock (26) so that the inside of the filter (2) is filled with the washing solution to increase spaces between the fibers, and then the 3-directional stopcock (26) is opened to pass the fluid toward a leukocyte-accommodating bag (24). Due to the increase in spaces between the fibers and the flow pressure of the washing solution, the leukocytes captured in spaces between the fibers in the filter (2) in the blood component-recovering apparatus (20) are washed with the washing solution, passed through the 3-directional stopcock (26), and recovered in the leukocyte-accommodating bag (24).

Hereinafter, one embodiment of the present invention is described with reference to Examples.

EXAMPLE 1

In the blood component-recovering apparatus shown in FIG. 1, filter (2) consists of a disk-shaped 3-layer nonwoven fabric (diameter 4.86 cm) of polyethylene terephthalate fibers. The three layers when the filter (2) is compressed to a predetermined volume by the pressing member (1) include a nonwoven fabric with a fiber diameter of 10 $\mu$m and a bulk density of 0.23 g/cm$^3$ in a first layer (upper layer), a nonwoven fabric with a fiber diameter of 3.5 $\mu$m and a bulk density of 0.11 g/cm$^3$ in a second layer (interlayer) and a nonwoven fabric with a fiber diameter of 1.5 $\mu$m and a bulk density of 0.12 g/cm$^3$ in a third layer (sublayer). The volume ratio of the layers was 30:22:48, and the total thickness was 8.1 mm. 100 ml bovine blood containing an ACD (acid citrate dextrose) solution as an anti-coagulation agent was passed therethrough at a flow rate of 5 ml/min. to capture leukocytes in the inside of the filter (2), while erythrocytes were passed through the bag filter (2) and recovered in the small blood bag (23). The yield of erythrocytes recovered in the small blood bag (23) was 95%, and the yield of platelets therein was 19%. Then, the 3-directional stopcock (26) was closed and the grasping portion (27) in FIG. 1 was then rotated in the opposite direction to transfer the pressing member (1) upward. Thereafter, the filter (2) was filled with physiological saline to increase spaces between the fibers, and then 150 ml physiological saline was passed at a flow rate of 5 ml/min. through the filtration portion (3) and recovered in the leukocyte-accommodating bag (24). The ratio of expansion of the filtration portion (3) charged with the filter (2), due to upward transfer of the pressing member (1), and the yield of leukocytes recovered in the leukocyte-accommodating bag (24) are shown in Table 1.

The volume expansion ratio is the ratio of the distance between the bottom of the lower lid portion and the pressing member when their screw-engagement was loosened to transfer the pressing member upward/the thickness of the filter (2) before whole blood was passed through the filter (2) (distance between the bottom of the lower lid portion and the pressing member). The leukocyte recovery ratio is the ratio of the number of leukocytes in the physiological saline accommodated in the leukocyte-accommodating bag (24)/ the number of leukocytes in blood accommodated in the blood bag (21).

TABLE 1

| Volume expansion ratio (fold) | 0 | 1.17 | 1.28 | 1.41 | 1.50 |
|---|---|---|---|---|---|
| Leukocyte recovery ratio (%) | 45.1 | 80.6 | 83.2 | 85.0 | 86.7 |

As is evident from Table 1, the yield of leukocytes increases with an increasing volume expansion ratio.

EXAMPLE 2

After a nonwoven fabric with a fiber diameter of 10 μm and a nonwoven fabric with a fiber diameter of 1.5 μm were immersed in 0.25% 2-hydroxyethyl methacrylate/ diethylaminoethyl methacrylate copolymer in ethanol, the grasping portion (38) in the blood component-recovering apparatus in FIG. 2 was rotated to transfer the rod-shaped member (36) downward whereby the filter (32) comprising said nonwoven fabric with a fiber diameter of 10 μm as a first layer and said nonwoven fabric with a fiber diameter of 1.5 μm as a second layer was pressed. The 2-layer nonwoven fabric had the nonwoven fabric having a fiber diameter of 10 μm and a bulk density of 0.23 g/cm$^3$ as the first layer and the nonwoven fabric with a fiber diameter of 1.5 μm and a bulk density of 0.12 g/cm$^3$ as the second layer when the bag (31) was compressed to a predetermined volume by the pressing member (33). A disk-shaped filter (diameter 3.82 cm, thickness 8.6 mm) consisting of the first layer as the upper layer and the second layer as the sublayer (volume ratio 60:40) was accommodated in a low-density polyethylene bag (31) in the blood component-recovering apparatus shown in FIG. 2.

50 ml umbilical cord blood containing a heparin solution as an anti-coagulation agent was passed therethrough at a flow rate of 5 ml/min. whereby leukocytes were captured in the filter, while erythrocytes and platelets were passed through the filter (32) and recovered in the small blood bag (23). The yield of erythrocytes recovered in the small blood bag (23) was 89% and the yield of platelets therein was 72%. Then, the 3-directional stopcock (26) was closed, and then the grasping portion (38) in FIG. 2 was rotated in the opposite direction to transfer the pressing member (33) upward. Thereafter, the bag (31) was filled with physiological saline to enlarge spaces between the fibers, and 120 ml physiological saline was passed at a flow rate of 5 ml/min. through the bag (31) charged with the filter (32) and recovered via the blood flow outlet tube (43) in the leukocyte-accommodating bag (24). The volume expansion ratio of the bag (31), attained by upward transfer of the pressing member and the yield of leukocytes recovered in the leukocyte-accommodating bag (24) are shown in Table 2.

TABLE 2

| Volume expansion ratio (fold) | 0.00 | 1.18 | 1.33 | 1.49 | 1.61 |
|---|---|---|---|---|---|
| Leukocyte recovery ratio (%) | 27.7 | 66.3 | 71.5 | 76.2 | 78.8 |

As is evident from Table 2, the yield of leukocytes increases with an increasing volume expansion ratio.

As described above, the blood component-recovering apparatus of the present invention is an easily handled and compact apparatus by which leukocytes captured in the filter can be recovered in high yield.

Another example for carrying out the blood component-recovering method of the present invention is described with reference to the blood component-recovering apparatus shown in FIGS. 4 and 5.

Figure 4:
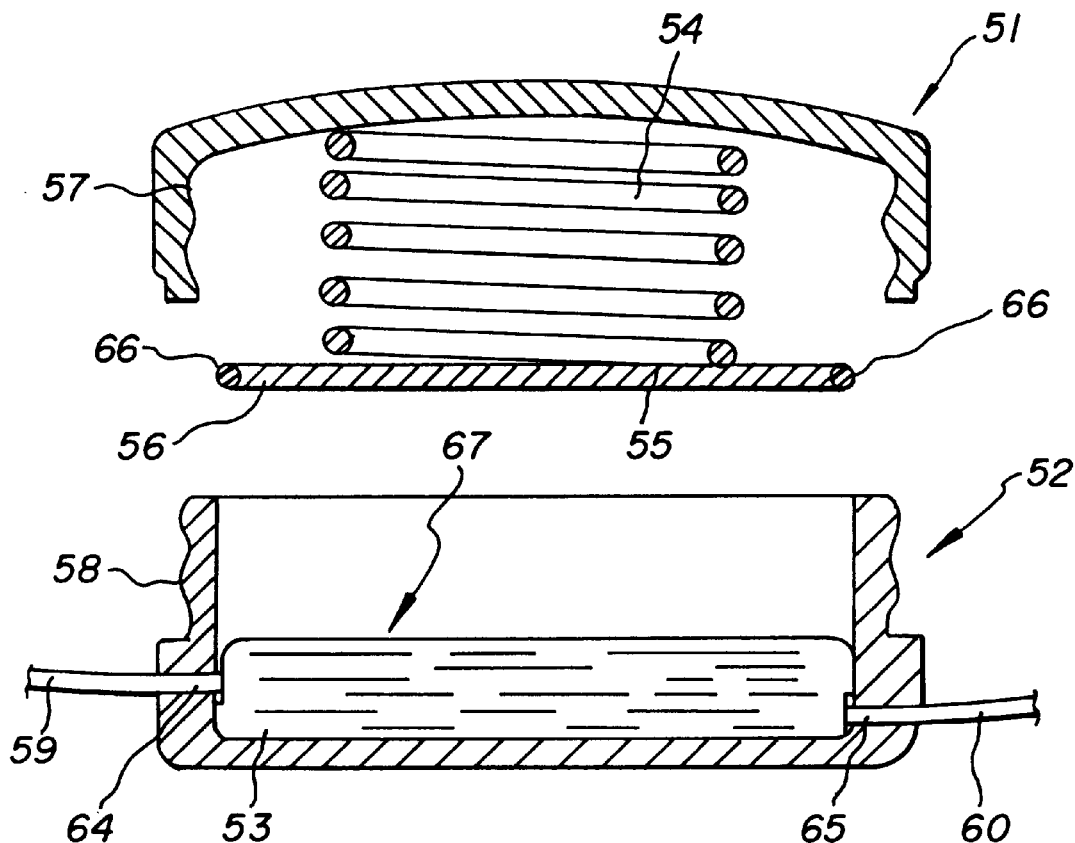
FIG. 4 is a schematic view of a blood component-recovering apparatus when the upper lid is separated from the lower lid.

FIG. 4 is a schematic view where an upper lid portion (51) is separated from a lower lid portion (52), and the lower lid portion (52) is provided with a filtration portion (67) accommodating a filter (53), and the sidewall of the lower lid portion (52) is provided with a blood flow inlet (64) and a blood flow outlet (65), and the upper lid portion (51) accommodates a spring body (54) for pressing the filter (53), the end (55) of the spring body (54) being connected to a pressing member (56) capable of being transferred to the inside of the lower lid portion (52). The pressing member (56) is shaped into a disk whose edge is provided with an O-ring (66) sliding liquid-tightly along the inner wall of the lower lid portion (52). A female screw (57) is formed on the inner wall of the opening of the upper lid portion (51), and a male screw (58) is formed on the outer wall of the opening of the lower lid portion, and as the male screw (58) is screw-engaged with the female screw (57), the spring body is compressed to press the pressing member (56) whereby the filter (53) is compressed.

Figure 5:
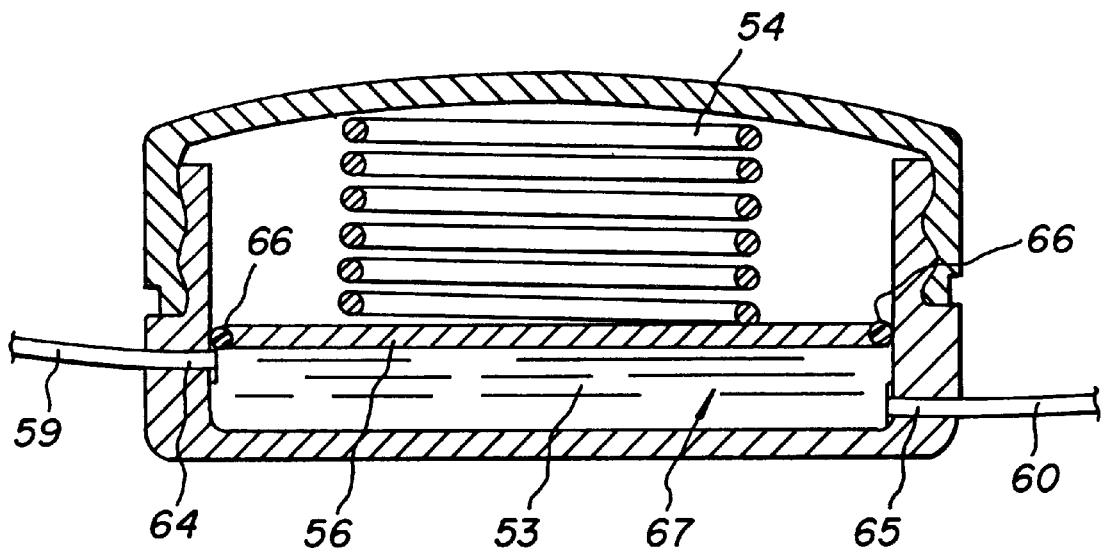
FIG. 5 is a schematic view of the blood component-recovering apparatus of FIG. 4 when the upper lid is screw-engaged with the lower lid.

FIG. 5 is a schematic view of the blood component-recovering apparatus where the upper lid portion (51) is completely screw-engaged with the lower lid portion (52).

The method of recovering leukocytes from human blood by use of the blood component-recovering apparatus where the upper lid portion (51) is completely screw-engaged with the lower lid portion (52) as shown in FIG. 5 is described with reference to FIG. 3 illustrating the method of collecting blood components.

From the blood bag (21) in which whole blood is accommodated, the whole blood is passed through the 3-directional stopcock (25) to the blood component-recovering apparatus (20) in FIG. 3, i.e., the whole blood is passed through a blood flow inlet tube 59 and introduced to the inside of the filter (53) from the blood flow inlet (64) in the blood component-recovering apparatus in FIG. 5 wherein the upper lid portion (51) is completely screw-engaged with the lower lid portion (52). Leukocytes in the filter material (53) are captured in the filter, e.g., spaces between the fibers therein, while erythrocytes are passed through the fiber aggregate and a flow outlet tube (60) in FIG. 5, and through the 3-directional stopcock (26), and are recovered in the small blood bag (23) in FIG. 3. The small blood bag (23) can also accommodate platelets in addition to erythrocytes, depending on the type of the filter material.

Then, the screw-engagement between the upper lid portion (51) and lower lid portion (52) in the blood component-recovering apparatus in FIG. 5 where the upper lid portion (51) is completely screw-engaged with the lower lid portion is loosened. By this loosing, the pressing member (56) moves upward so that the volume of the filtration portion

(67) charged with the filter (53) is increased. Thereafter, a washing solution in the washing bag (22) is passed through the 3-directional stopcock (25) into the blood component-recovering apparatus (20) in FIG. 3. In this step, it is preferable that introduction of the washing solution into the blood component-recovering apparatus (20) is temporarily stopped by the 3-directional stopcock (26) so that the inside of the filter (53) is filled with the washing solution to increase spaces between the fibers, and then the 3-directional stopcock (26) is opened to pass the fluid toward the leukocyte-accommodating bag (24). Due to the increase in spaces between the fibers and the flow pressure of the washing solution, the leukocytes captured in spaces between the fibers in the filter (53) in the blood component-recovering apparatus (20) are washed with the washing solution, passed through the 3-directional stopcock (26), and recovered in the blood-recovering bag (24).

In FIG. 4, the pressing member (56) connected to the end (55) of the spring body (54) is accommodated in the upper lid portion (51). Another example is a blood component-recovering apparatus in which the pressing member (56) is separated from the spring body (54) and placed on the filter (53). In this apparatus, as the upper lid portion (51) is screw-engaged with the lower lid portion (52), the spring body (54) presses the pressing member (56). In this apparatus, because the pressing member (56) is previously provided liquid-tightly with the O-ring (66) on the inner wall of the lower lid portion (52), it is not necessary to fit the pressing member (56) to the inner wall of the lower lid portion (52).

Figure 6:
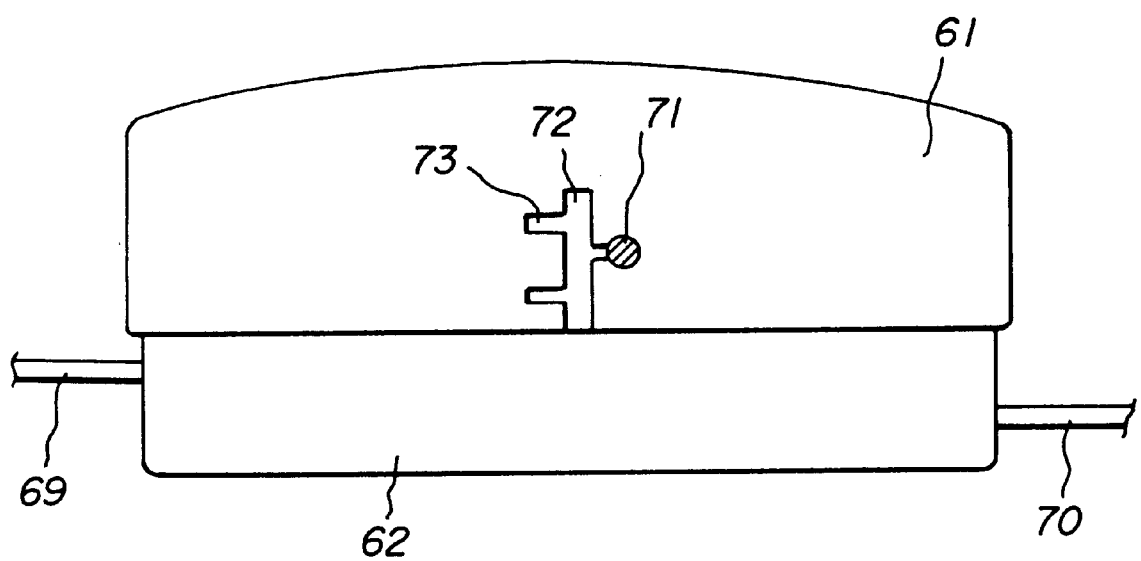
FIG. 6 is a view of a blood component-recovering apparatus showing another embodiment of the present invention.

FIG. 6 is another example of the blood component-recovering apparatus of the present invention where the upper lid portion (61) is set to the lower lid portion (62). The outer wall of the lower lid portion (62) is provided with a protruding portion (71), and the sidewall of the upper lid portion (61) is provided with a hole portion consisting of a lengthwise long hole (72) extending in a lengthwise direction and three crosswise long holes (73) communicating with said lengthwise long hole (72), where the protruding portion (71) slides along the lengthwise long hole (72) and is locked with the crosswise long holes (73). Hole portions are formed preferably on the sidewall of the upper lid portion (61) and in opposite positions to each other. The protruding portions (71) are formed preferably in opposite positions to each other on the outer wall of the lower lid portion (62). The inside of the blood component-recovering apparatus consisting of the upper lid portion (61) and the lower lid portion (62) is the same as in FIG. 4 except for the male screw (58) and the female screw (57) and is formed by screw-engaging the upper lid portion (61) with the lower lid portion (62) in FIG. 6.

In another example of the blood component-recovering apparatus of the present invention, the filter (53) is accommodated in a bag made of flexible resin, and the blood flow inlet tube (59) and the blood flow outlet tube (60) are connected to the bag and arranged in the filtration portion (67) in the lower lid portion (52) in FIG. 4. The blood flow inlet tube (59) extends from the blood flow inlet (64) in FIG. 4 to the outside of the blood component-recovering apparatus, and the blood flow outlet tube (60) extends from the blood flow outlet (65) to the outside of the blood component-recovering apparatus. In FIG. 4, the pressing member (56) is provided at the edge thereof with the O-ring (66), and the O-ring (66) slides liquid-tightly along the inner wall of the lower lid portion (52), thus preventing blood components in the filtration portion (67) from leaking into the upper lid portion (51), but if the filter (53) is accommodated in a bag, it is not always necessary for the edge of the pressing member (56) to slide liquid-tightly along the inner wall of the lower lid portion (52), so the O-ring (66) may be absent.

EXAMPLE 3

In the blood component-recovering apparatus shown in FIG. 4, filter (53) consists of a disk-shaped 3-layer nonwoven fabric (diameter 4.86 cm) of polyethylene terephthalate fibers. The three layers (FIG. 5) when the filter (53) is compressed to a predetermined volume by the pressing member (56) has a nonwoven fabric with a fiber diameter of 10 $\mu$m and a bulk density of 0.23 g/cm$^3$ in a first layer (upper layer), a nonwoven fabric with a fiber diameter of 3.5 $\mu$m and a bulk density of 0.11 g/cm$^3$ in a second layer (interlayer) and a nonwoven fabric with a fiber diameter of 1.5 $\mu$m and a bulk density of 0.12 g/cm$^3$ in a third layer (sublayer). The weight volume ratio was 30:22:48, and the total thickness was 8.3 mm. 100 ml bovine blood containing an ACD solution as an anti-coagulation agent was passed therethrough at a flow rate of 5 ml/min. to capture leukocytes in the inside of the filter (53), while erythrocytes were passed through the filter (53) and recovered in the small blood bag (23). The yield of erythrocytes recovered in the small blood bag (23) was 97%, and the yield of platelets therein was 18%. Then, the 3-directional stopcock (26) was closed and then the engagement between the upper lid portion (51) and the lower lid portion (52) in FIG. 5 was loosened to transfer the pressing member (56) upward. Thereafter, the filter (53) was filled with physiological saline to increase spaces between the fibers, and then 150 ml physiological saline was passed at a flow rate of 5 ml/min. through the filtration portion (67) and recovered in the leukocyte-accommodating bag (24). The expansion ratio of the filtration portion (67) charged with filter (53), attained by upward transfer of the pressing member (56), and the recovery ratio of leukocytes recovered in the leukocyte-accommodating bag (24) are shown in Table 3.

The volume expansion ratio is the ratio of the distance between the bottom of the lower lid portion and the pressing member when their screw-engagement was loosened to transfer the pressing member upward/the thickness of the filter (53) when the upper lid portion (51) was completely screw-engaged with the lower lid portion (52) (distance between the bottom of the lower lid portion and the pressing member). The leukocyte recovery ratio is the ratio of the number of leukocytes in the physiological saline accommodated in the leukocyte-accommodating bag (24)/the number of leukocytes in blood accommodated in the blood bag (21).

TABLE 3

| Volume expansion ratio (fold) | 0.00 | 1.06 | 1.14 | 1.32 | 1.53 | 1.73 | 1.92 |
|---|---|---|---|---|---|---|---|
| Leukocyte recovery ratio (%) | 47.2 | 78.7 | 82.1 | 87.7 | 89.8 | 91.9 | 93.3 |

As is evident from Table 3, the yield of leukocytes increases with an increasing volume expansion ratio.

EXAMPLE 4

A nonwoven fabric with a fiber diameter of 10 $\mu$m and a nonwoven fabric with a fiber diameter of 1.5 $\mu$m were immersed in 0.25% 2-hydroxyethyl methacrylate/diethylaminoethyl methacrylate copolymer in ethanol. The protruding portion (71) of the lower lid portion (62) of the blood-recovering apparatus shown in FIG. 6 was locked at the uppermost crosswise long hole (73) of the upper lid portion (61) to fit the upper lid portion (61) to the lower lid portion (62) thereby compressing the filter by the pressing member. After compression, a disk-shaped, 2-layer filter (diameter 3.82 cm) had the nonwoven fabric having a fiber diameter of 10 μm and a bulk density of 0.23 g/cm³ as an upper layer (first layer) and the nonwoven fabric with a fiber diameter of 1.5 μm and a bulk density of 0.12 g/cm³ as a sublayer (second layer). This filter was arranged in the filtration portion in the apparatus shown in FIG. 6. The thickness of the filter when the protruding portion (71) was placed at the uppermost crosswise long hole (73) was 9.7 mm.

100 ml human blood containing a heparin solution as an anti-coagulation agent was passed therethrough at a flow rate of 5 ml/min. whereby leukocytes were captured in the filter material, while erythrocytes and platelets were passed through the filter and recovered in the small blood bag (23). The yield of erythrocytes recovered in the small blood bag (23) was 95% and the yield of platelets therein was 88%. Then, the 3-directional stopcock (26) was closed, and then the protruding portion (71) in FIG. 6 was transferred to the lowermost crosswise long hole (73) to increase the volume of the filtration portion. Thereafter, the filtration portion was filled with physiological saline to enlarge spaces between the fibers, and 150 ml physiological saline was passed through the filtration portion at a flow rate of 5 ml/min. and recovered in the leukocyte-accommodating bag (24). The volume expansion ratio of the filtration portion, attained by upward transfer of the protruding portion (71) to the crosswise long hole (73), and the yield of leukocytes recovered in the leukocyte-accommodating bag (24) were determined. The distance between the lowermost crosswise long hole and the middle crosswise long hole was 6.4 mm and the distance between the lowermost crosswise long hole and the uppermost crosswise long hole was 12.3 mm. When the protruding portion was placed at the middle crosswise long hole (volume expansion ratio, 1.66), the yield of leukocytes was 92.3%, and when the protruding portion was placed at the lowermost crosswise long hole (volume expansion ratio, 2.77), the yield of leukocytes was 94.7%

EXAMPLE 5

The blood component-recovering apparatus in FIG. 5 was used, and the filter in Example 4 (diameter 3.82 cm, thickness 8.6 mm) was used. 50 ml umbilical cord blood containing a heparin solution as an anti-coagulation agent was passed therethrough at a flow rate of 5 ml/min. whereby leukocytes were captured in the filter, while erythrocytes and platelets were passed through the filter and recovered in the small blood bag (23). The yield of erythrocytes recovered in the small blood bag (23) was 91% and the yield of platelets therein was 75%. Then, the 3-directional stopcock (26) was closed, and then the engagement between the upper lid portion and the lower lid portion in FIG. 5 was loosened to transfer the pressing member upward. Thereafter, the filtration portion (67) was filled with physiological saline to enlarge spaces between the fibers, and 150 ml physiological saline was passed through the filtration portion (67) at a flow rate of 5 ml/min. and recovered in the leukocyte-accommodating bag (24). The volume expansion ratio of the filtration portion (67), attained by upward transfer of the pressing member, and the yield of leukocytes recovered in the leukocyte-accommodating bag (24) are shown in Table 4.

TABLE 4

| Volume expansion ratio (fold) | 1.00 | 1.13 | 1.37 | 1.54 | 1.78 | 1.91 |
|---|---|---|---|---|---|---|
| Leukocyte recovery ratio (%) | 30.4 | 69.3 | 74.1 | 79.5 | 81.8 | 82.9 |

According to the method of the present invention, leukocytes captured in the filter could be recovered in high yield. Further, the apparatus of the present invention is an easily handled and compact apparatus and suitable for carrying out the method of the present invention.

EXAMPLE 6

In the blood component-recovering apparatus shown in FIG. 1, the filter consisting of disk-shaped 2-layer fibrous aggregates (diameter 5.6 cm) of polyethylene terephthalate fibers was used. The two layers have two sheets of nonwoven fabric with a fiber diameter of 10 μm and a thickness of 0.82 mm in an upper layer and 30 sheets of nonwoven fabric with a fiber diameter of 3.5 μm and a thickness of 0.38 mm in a lower layer. When the filter was compressed by the pressing member, the bulk density of the filter was 0.19 g/cm³.

120 ml bovine blood containing an ACD solution as an anti-coagulation agent was passed through the filter from the blood flow inlet to the blood flow outlet at a flow rate of 5 ml/min. to capture leukocytes in the inside of the filter, while erythrocytes were passed through the filter. Then, 40 ml of physiological saline solution was passed through the filter to wash out erythrocytes and platelets remaining in the filter and the inner volume of the filter was enlarged to have a bulk density of 0.11 g/cm³ and then 80 ml physiological saline solution containing bovine serum albumin was passed through the filter to recover leukocytes. In comparison, the inner volume of the filter was not changed and the washing solution and the physiological saline solution were passed through the filter to recover leukocytes in the same manner as in the above method.

The yields of leukocytes recovered are shown in Table 5.

TABLE 5

| Bulk density (g/cm³) | | Yield of leukocytes |
|---|---|---|
| Captured | Recovered | (%) |
| 0.19 | 0.11 | 61.69 ± 2.57 |
| 0.19 | 0.19 | 55.79 ± 2.22 |

EXAMPLE 7

50 ml bovine blood containing an ACD solution was passed through the filter in the same manner as in Example 6. The yields of leukocytes recovered are shown in Table 6.

TABLE 6

| Bulk density (g/cm³) | | Yield of leukocytes |
|---|---|---|
| Captured | Recovered | (%) |
| 0.19 | 0.11 | 73.44 ± 2.01 |
| 0.19 | 0.19 | 66.22 ± 1.50 |

The meanings of the numerals in the drawings are as follows:

1, 33, 56: pressing members
2, 32, 53: filters 3, 67: filtration portion
4, 30: housings
5, 36: rod-shaped members
6: concave portion
7, 37: head of the bolt
8: nut portion
9: female screw
10, 44, 64: blood flow inlet
11, 45, 65: blood flow outlet
12, 42, 59, 69: blood inlet tubes
13, 43, 60, 70: blood flow outlet tubes
14, 51, 61: upper lid portion
15, 52, 62: lower lid portion
16, 39, 58: male screw
17, 57: female screw
18, 66: o-ring
19: hole
20: blood component-recovering apparatus
21: blood bag
22: washing solution bag
23: small blood bag
24: leukocyte-accommodating bag
25, 26: 3-directional stopcock
27, 38: grasping portions
31: bag
34: chamber
35: lock portion
40: second hole
41: first hole
54: spring body
55: end of the spring body
71: protruding portion
72: lengthwise long hole
73: crosswise long hole

What is claimed is:

1. A blood component-recovering apparatus comprising a housing in which is accommodated (a) a filtration portion charged with (b) a filter which is capable of passing erythrocytes but of capturing leukocytes and (c) a pressing member for pressing said filter, said housing being provided in the sidewall thereof with (d) a blood flow inlet and (e) a blood flow outlet communicating with said filtration portion.

2. The blood component-recovering apparatus of claim 1, wherein the housing is provided in the upper wall thereof with (f) a means capable of moving the pressing member in a vertical direction.

3. The blood component-recovering apparatus of claim 1, wherein (c) the pressing member is capable of being arranged in a downward position while a blood containing blood components is passed through the filtration portion, and of being transferred to an upward position to increase the volume of said filtration portion, and to allow a washing solution to be passed through said filter to recover leukocytes.

4. The blood component-recovering apparatus according to claim 1, wherein (f) the means capable of moving the pressing member in a vertiacl direction comprises (g) a bolt portion including (h) a rod-shaped member having (i) a male screw formed on the sidewall thereof extending in a longitudinal direction above the pressing member; (j) a hole through which the rod-shaped member can be transferred vertically and being formed in the bottom of (k) a concave portion provided on the upper wall of the housing; and (l) a nut portion comprising a cylinder portion and a grasping portion, said cylinder portion having (m) a female screw formed on the inner wall thereof and having an outer diameter which permits said cylinder portion to be inserted into said concave portion and being capable of being screw-engaged with the male screw in said bolt portion.

5. The blood component-recovering apparatus according to claim 1, wherein (f) the means capable of moving the pressing member in a vertical direction comprises (n) a rod-shaped member extending in a longitudinal direction above the pressing member and having (o) a lock portion at the bottom and (p) a male screw formed on the sidewall thereof; (q) a chamber provided on the pressing member, having (r) a first hole through which said rod-shaped member penetrates and accommodating said lock portion; and (s) a female screw formed on the inner wall of (t) a second hole provided on the upper wall of housing and being capable of being screw-engaged with the male screw of said rod-shaped member.

6. The blood component-recovering apparatus according to claim 4 or 5, wherein the pressing member is in the form of a disk provided in a side edge thereof with (u) an O-ring capable of sliding liquidtightly along the inner wall of the housing.

7. The blood component-recovering apparatus according to claim 1, wherein the housing comprises (v) an upper lid portion and (w) a lower lid portion.

8. The blood component-recovering apparatus according to claim 7, wherein (v) said upper lid portion accommodates (x) a spring body for pressing (a) said filtration portion and (c) said pressing member is connected to the end of said spring body and is capable of being positioned in the inside of (w) said lower lid portion, and (w) said lower lid portion accommodates said filter, is provided with (d) a blood inlet and (e) a blood outlet and is engageable with the upper lid portion.

9. The blood component-recovering apparatus according to claim 7, wherein (v) said upper lid portion accommodates (x) a spring body for pressing (a) said filtration portion, and (w) siad lower lid portion accommodates (b) said filtration portion and (c) a pressing member arranged on the filtration portion and is provided with (d) a blood inlet and (e) a blood outlet and is engageable with the upper lid portion.

10. The blood component-recovering apparatus according to claim 9 or 10, wherein an outer wall of the lower lid portion is provided with a protruding portion, and a sidewall of the upper lid portion is provided with a hole portion consisting of a first hole extending lengthwise in a longitudinal direction and at least one second hole extending lengthwise in a latitudinal direction to and communicating with said lengthwise long hole, and the protruding portion being slideable along said first hole and of being locked with said second hole.

11. The blood component-recovering apparatus according to claim 1, wherein the filter is accommodated in a bag made of flexible resin, and said bag is connected to a blood flow inlet tube and a blood flow outlet tube.

12. The blood component-recovering apparatus according to claim 1, wherein the filter comprises a fiber aggregate of fibers having a fiber diameter of 25 $\mu$m or less said fiber aggregate having a bulk density of 0.05 to 0.50 g/cm$^3$.

13. The blood component-recovering apparatus according to claim 1, wherein the filter comprises a multi-layer fiber aggregate, and at least one layer comprises a fiber aggregate of fibers having a fiber diameter of 25 $\mu$m or less said fiber aggregate having a bulk density of 0.05 to 0.50 g/cm$^3$.

14. The blood component-recovering apparatus according to claim 1, wherein the inner volume of the filtration portion in the blood component-recovering apparatus when said pressing means is in an upward position is at least 1.10-fold relative to the inner volume of the filtration portion when said pressing means is in a downward position.

15. A method of recovering blood components, which comprises passing a blood containing blood components through a filtration portion charged with a filter which is capable of passing erythrocytes but capturing leukocytes, thereafter enlarging the inner volume of said filtration portion, and then passing a washing solution through said filtration portion to recover leukocytes.

16. The method of recovering blood components according to claim 15, wherein the filter is accommodated in a bag made of flexible resin and said bag is connected to a blood inlet tube and a blood outlet tube.

17. The method of recovering blood components according to claim 15, wherein the filter comprises a fiber aggregate of fibers having a fiber diameter of 25 µm or less, said fiber aggregate having a bulk density of 0.05 to 0.50 g/cm$^3$.

18. The method of recovering blood components according to claim 15, wherein the filter comprises a multi-layer fiber aggregate, and at least one layer comprises a fiber aggregate of fibers having a fiber diameter of 25 µm or less said fiber aggregate having a bulk density of 0.05 to 0.50 g/cm$^3$.

19. The method of recovering blood components according to claim 15, wherein the inner volume of the filtration portion in the blood component-recovering apparatus after being enlarged is at least 1.10-fold relative to the inner volume of the filtration portion before blood is passed through the blood component-recovering apparatus.

20. The method of recovering blood components according to claim 15, wherein said blood is umbilical cord blood.

* * * * *